(12) United States Patent
St. Germain et al.

(10) Patent No.: US 6,261,315 B1
(45) Date of Patent: *Jul. 17, 2001

(54) TUBULAR BODY STRUCTURE MARKING METHODS AND APPARATUS

(75) Inventors: Jon Patrick St. Germain, Elk River; Todd Allen Berg, Lino Lakes, both of MN (US)

(73) Assignee: St. Jude Medical Cardiovascular Group, Inc., Minneapolis, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/958,461

(22) Filed: Oct. 28, 1997

(51) Int. Cl.$^7$ ........................................................ A61F 2/00
(52) U.S. Cl. ................................................. 623/1.11
(58) Field of Search ................... 623/1, 11, 12, 623/1.11, 1.14; 600/502; 128/899; 606/116, 130, 190, 194

(56) References Cited

U.S. PATENT DOCUMENTS

| | | | |
|---|---|---|---|
| 3,999,551 | * 12/1976 | Spitz et al. | 606/190 |
| 4,041,931 | * 8/1977 | Elliott et al. | |
| 4,202,349 | 5/1980 | Jones | 128/689 |
| 4,418,693 | * 12/1983 | LeVeen et al. | 606/190 |
| 5,059,197 | * 10/1991 | Urie et al. | 606/116 |
| 5,112,340 | * 5/1992 | Krenkel et al. | 606/130 |
| 5,197,482 | * 3/1993 | Rank et al. | 606/116 |
| 5,221,269 | * 6/1993 | Miller et al. | 606/116 |
| 5,320,100 | * 6/1994 | Herweck et al. | 623/1 |
| 5,354,279 | 10/1994 | Holfling | 604/164 |
| 5,380,290 | * 1/1995 | Makower et al. | 604/164 |
| 5,387,235 | * 2/1995 | Chuter | 623/1 |
| 5,441,517 | * 8/1995 | Kensey et al. | 606/213 |
| 5,456,718 | * 10/1995 | Szymaitis | 623/11 |
| 5,496,365 | * 3/1996 | Srgo | 623/1 |
| 5,500,000 | * 3/1996 | Feagin et al. | 606/213 |
| 5,531,741 | * 7/1996 | Barbacci | 606/153 |
| 5,755,714 | * 5/1998 | Murphy-Chutorian | 606/15 |
| 5,853,366 | * 12/1998 | Dowlatshahi | 606/116 |
| 5,916,194 | * 6/1999 | Jacobsen et al. | 604/96 |

FOREIGN PATENT DOCUMENTS

| | | | |
|---|---|---|---|
| 0 393 972 A1 | 10/1990 | (EP) | A61B/17/34 |
| 0 416 793 A1 | 3/1991 | (EP) | A61F/17/22 |
| WO 96/32892 | 10/1996 | (WO) | A61B/17/00 |

* cited by examiner

*Primary Examiner*—Michael J. Milano
(74) *Attorney, Agent, or Firm*—Fish & Neave; Robert R. Jackson; Brajesh Mohan

(57) ABSTRACT

To facilitate subsequent location of a point along a patient's tubular body structure (e.g., a circulatory system vessel), a marker structure is inserted into and along the lumen of that tubular body structure. At the desired point along the lumen, a distal portion of the marker structure is made to pass out through a side wall of the tubular body structure so that it projects from that side wall and visibly and/or radiologically marks the desired point along the tubular body structure. The marker structure may also be used as an anchor for other instrumentation brought up to the outside of the tubular body structure (e.g., for use in further treatment of the tubular body structure).

26 Claims, 4 Drawing Sheets

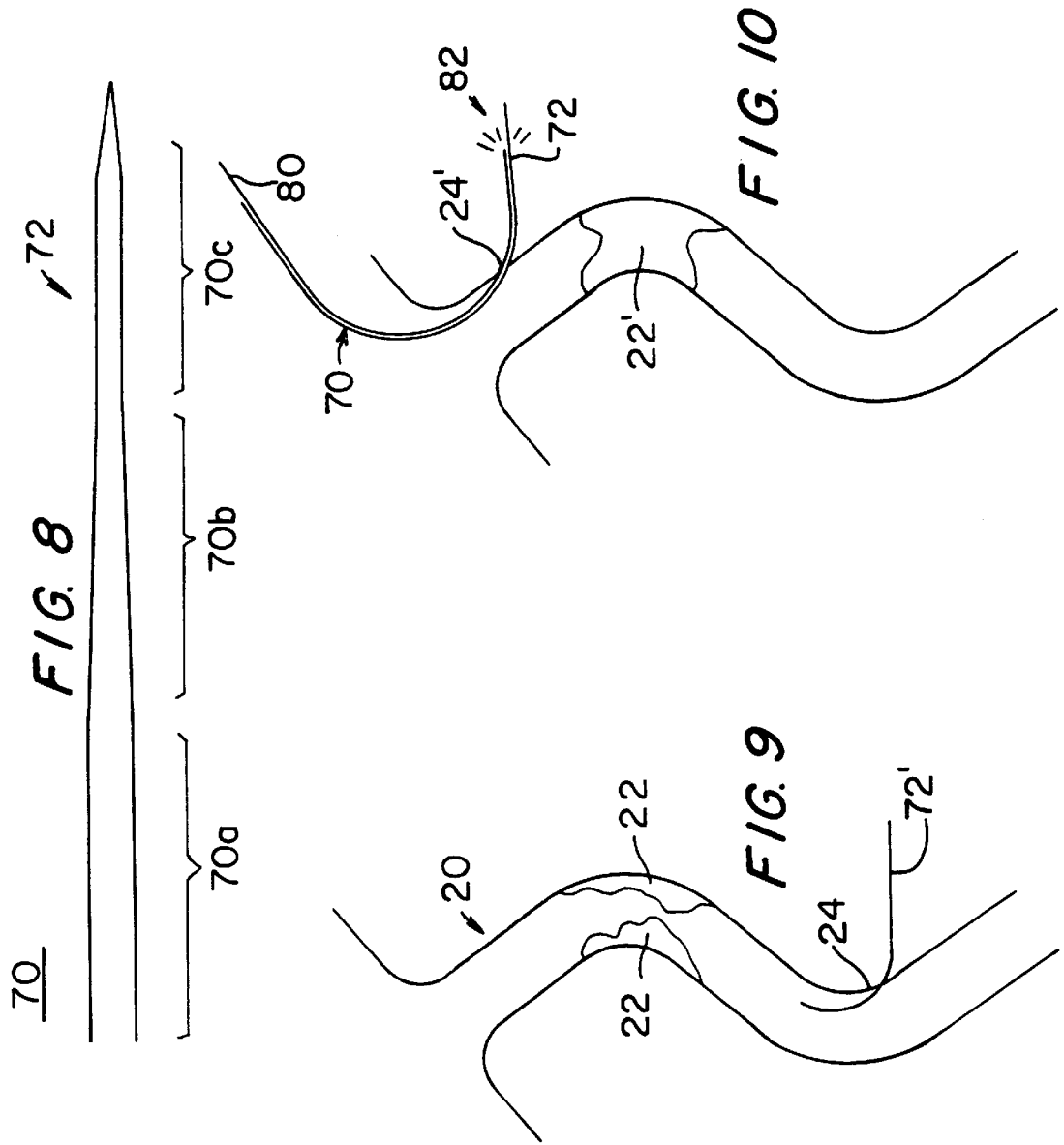

US 6,261,315 B1

TUBULAR BODY STRUCTURE MARKING METHODS AND APPARATUS

BACKGROUND OF THE INVENTION

This invention relates to treatment of a patient's tubular body structures, and more particularly to facilitating location of treatment sites along such structures.

A variety of medical treatments involve needing to know a point along a patient's tubular body structure at which a treatment step is to be performed. As just one example of this, a tubular bypass graft may need to be installed in a patient's circulatory system. It may be difficult from outside the circulatory system tissue (and possibly other associated tissue) to find the exact location or locations at which either or both ends of the bypass graft should be attached. For example, one or both of these points may be located remotely and relatively inaccessibly in the patient where it is difficult to see. Alternatively or additionally, at one or both of these points the patient's circulatory system tubing may be surrounded by or embedded in other tissue such as fat or the myocardium. The recent trend toward less invasive treatments may increase the difficulty experienced by the physician in locating the point or points along the patient's body tubing at which treatment steps are to be performed.

In view of the foregoing, it is an object of this invention to provide methods and apparatus for facilitating the location of medical treatment sites along a patient's tubular body structures.

SUMMARY OF THE INVENTION

This and other objects of the invention are accomplished in accordance with the principles of the invention by providing methods and apparatus for placing a longitudinal marker structure through a side wall of a patient's tubular body structure. The marker is preferably placed through the side wall of the tubular body structure from inside that structure. The marker preferably extends out of the side wall of the tubular body structure through any adjacent tissue. The marker may be introduced into the patient through a catheter or catheter-like instrumentation that has been inserted longitudinally into the patient along lumens of the patient's tubular body structure. The catheter or catheter-like apparatus may include a distal portion for deflecting a distal portion of the marker structure laterally toward the side wall of the tubular body structure where the marker is to pass through that side wall. The marker is preferably small in cross section and sharply pointed so that it can pass through the side wall tissue but without making a large hole that will leak or be slow to heal if necessary. The marker is preferably adapted for good visibility by whatever means are employed to observe it. For example, the marker may be made radio-opaque for good radiologic (e.g., X-ray or fluoroscopic) observation. The marker may be brightly colored or fluorescent, or may even include a visible light source (e.g., via fiber optics) to facilitate visual detection of the marker. The marker may always remain attached to instrumentation that extends proximally out of the patient so that the marker can be removed from the patient at any time. Alternatively, the marker may be selectively detachable from the instrumentation that is used to install it so that the marker can be left in place in the patient for subsequent use after the instrumentation that was used to install it has been removed from the patient.

A possible additional use of the markers of this invention is as an anchor or stabilizer for other apparatus to be used in treating the patient.

Further features of the invention, its nature and various advantages will be more apparent from the accompanying drawings and the following detailed description of the preferred embodiments.

BRIEF DESCRIPTION OF THE DRAWINGS

FIG. 8 is a simplified elevational view of representative portions of an illustrative embodiment of apparatus in accordance with the invention.

FIG. 9 is another view similar to FIG. 4 showing another illustrative embodiment of the invention.

FIG. 10 is still another view somewhat similar to FIG. 9 showing another illustrative use of the invention.

DETAILED DESCRIPTION OF THE PREFERRED EMBODIMENTS

Goldsteen et al. U.S. patent application Ser. No. 08/745,618, filed Nov. 7, 1996, shows medical procedures and apparatus which can be used to install a bypass conduit in a patient's internal tubular body structure, with most or all of the work being performed remotely through lumens of the patient's tubular body structures and therefore without surgically opening the patient. Other somewhat related procedures are shown in Sullivan et al. U.S. patent application Ser. No. 08/844,992, filed Apr. 23, 1997, and Sullivan et al. U.S. patent application Ser. No. 08/869,808, filed Jun. 5, 1997. All three of these references are hereby incorporated by reference herein.

The various procedures shown in the three references mentioned above may include a need to make a connection to the side wall of a patient's tubular body conduit from the outside of that conduit. (For convenience herein it will sometimes be assumed that the conduit is a blood vessel. However, it will be understood that the invention is equally applicable to any other type of tubular body conduit.) Moreover, this connection must generally be made at a particular point along the tubular conduit (e.g., just downstream from a blockage in that conduit) and under conditions of limited visibility (e.g., because the procedure is being performed remotely inside a patient whose body has not been opened surgically). Still another difficulty may be the presence of other tissues (e.g., the myocardium or fat) covering the point at which it is desired to make the connection to the tubular conduit.

Figure 1:
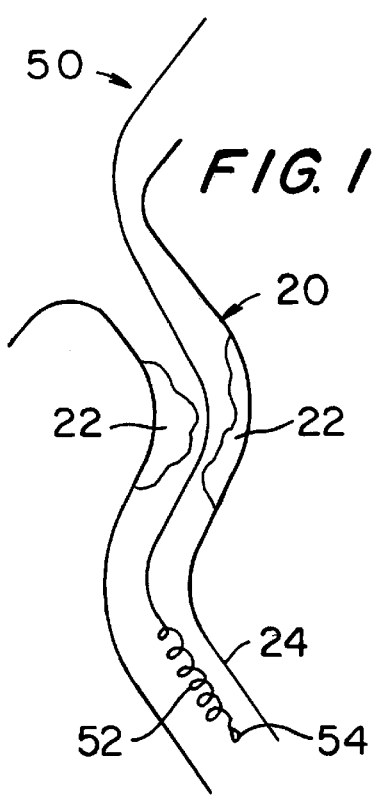
FIG. 1 is a simplified sectional view showing an early stage in an illustrative procedure in accordance with this invention. Illustrative apparatus usable in accordance with the invention is shown in FIG. 1.
Figure 5:
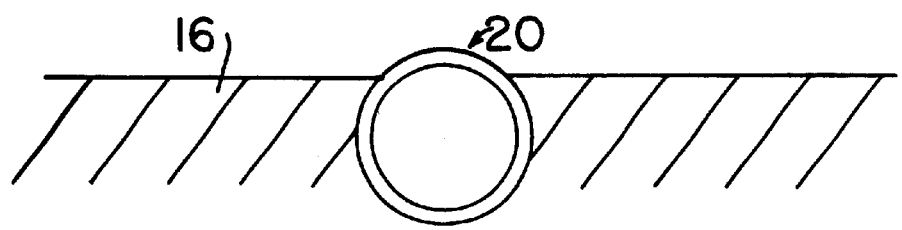
FIG. 5 is a simplified sectional view of typical body tissue structures that are treatable in accordance with the invention.
Figure 6:
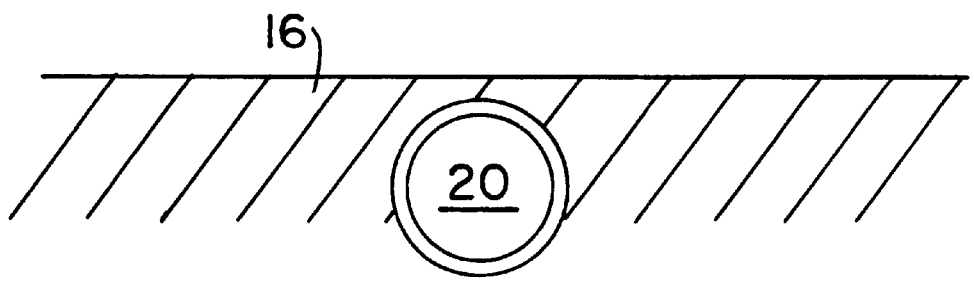
FIG. 6 is another view similar to FIG. 5 showing other typical body tissue structures that are treatable in accordance with the invention.
Figure 7:
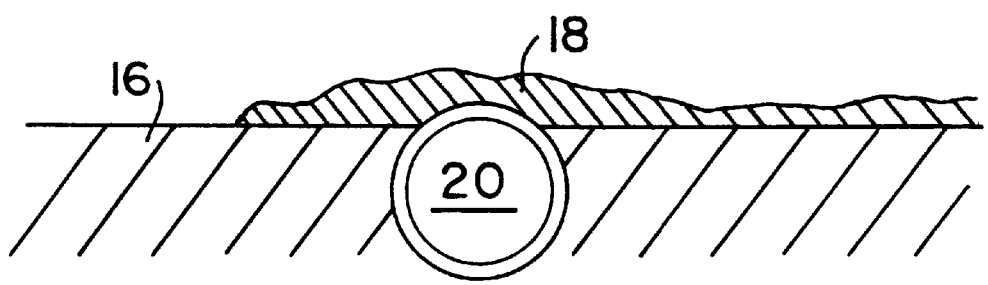
FIG. 7 is another view similar to FIGS. 5 and 6 showing still other typical body tissue structures that are treatable in accordance with the invention.

Methods and apparatus in accordance with this invention for facilitating making connections such as the ones described above (or for performing any other desired treatment at a particular location along a patient's tubular body conduit) are illustrated beginning with FIG. 1. In FIG. 1 it is desired to make a connection to the side wall of coronary artery 20 at location 24 which is downstream from blockage 22 in that artery. Although FIG. 1 suggests that the side wall of artery 20 may be quite exposed on the outside of the heart, the artery may in fact be partly or wholly embedded in other tissue such as the myocardium 16 as shown in FIGS. 5 and 6, or the vessel may be obscured by fat 18 which is on or around the heart as shown in FIG. 7. It may therefore sometimes be difficult to find a desired treatment site along artery 20 from outside the artery and the surrounding tissue.

Using the illustrative methods and apparatus shown beginning with FIG. 1, a guide structure 50 is first inserted into and along lumens of the patient's circulatory system from a remote location such as a femoral (leg) artery of the patient. The distal portion of guide structure 50 (which includes distal spring coil 52 and distal-most tip 54) is inserted along the circulatory system lumens until it enters coronary artery 20, passes through obstruction 22, and extends approximately to or beyond location 24. Guide structure 50 may be similar to guide structures ("guide wires") that are conventionally used to guide angioplasty balloon catheters or other similar apparatus into a patient's circulatory system tubing. Guide structure 50 or key portions thereof may be radiologically viewable to facilitate radiologic observation of the progress of structure 50 into the patient and/or the final positioning of structure 50 in the patient.

Figure 2:
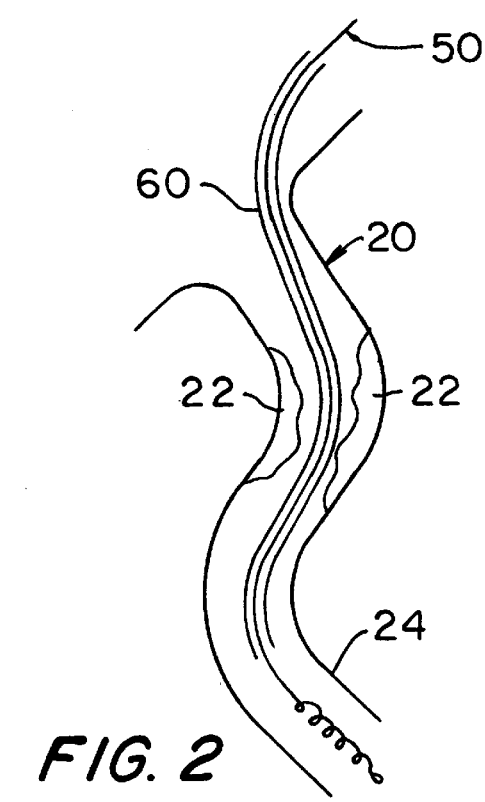
FIG. 2 is another view similar to FIG. 1 showing a later stage in use of the illustrative procedure and apparatus in accordance with the invention.

After guide structure 50 has been positioned in the patient as shown in FIG. 1, tubular structure 60 is inserted into the patient along and around guide structure 50 until a distal portion of structure 60 is adjacent to location 24 as shown in FIG. 2. Tubular structure 60 may be a catheter or catheter-like structure, and for convenience may be sometimes referred to herein as a catheter. Structure 60 may be wholly or partly radiologically viewable for purposes similar to the above-described radiologic viewability of structure 50. Alternatively or additionally, structure 60 may be usable to convey and release radiologically (e.g., fluoroscopically) viewable liquid, again for purposes similar to the above-described radiologic viewability of structure 50.

Figure 3:
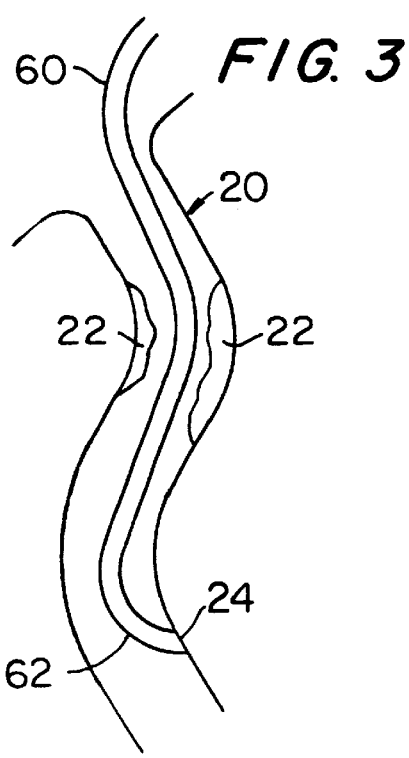
FIG. 3 is another view similar to FIG. 1 showing a still later stage in use of the illustrative procedure and apparatus in accordance with the invention.

After catheter 60 is in place in the patient, guide structure 50 may be proximally withdrawn from catheter 60 and from the patient. The distal portion 62 of catheter 60 may then be arcuately deflected toward the side wall of artery 20 at location 24 as shown in FIG. 3. It will be understood that this deflection of distal portion 62 is transverse to the longitudinal axis of artery 20. Any of several techniques may be used to produce this transverse, arcuate deflection. For example, distal portion 62 may be resiliently biased to deflect as shown in FIG. 3 and may be prevented from doing so as long as guide structure 50 is disposed in structure 60. As soon as guide structure 50 is withdrawn, however, distal portion 62 automatically curves to one side as shown in FIG. 3. As another example, distal portion 62 may be deflected to one side by one or more pull wires disposed in or on the wall of structure 60. As still another example, technology of the type shown in Bachinski et al. U.S. patent application Ser. No. 08/842,391, filed Apr. 23, 1997 (which is also hereby incorporated by reference herein), may be used to selectively curve the distal portion 62 of structure 60.

Catheter 60 may include a structure for selectively occluding vessel 20 to control blood flow along the vessel. For example, a selectively inflatable balloon may be provided around the outside of catheter 60 for stopping blood flow along vessel 20 when the balloon is inflated. The construction of the catheter shaft can include a polytetrafluoroethylene inner liner for optimal wire movement, and an internal braid for torque control and push strength. Catheter 60 may also contain a proximal curve, which matches the curvature of the heart, to orientate the catheter deflection perpendicular to the heart wall. To enable catheter 60 to extend into small and sharply curved body conduits, catheter 60 may be made with a relatively small cross section and may in that case be referred to as a micro-catheter.

Figure 4:
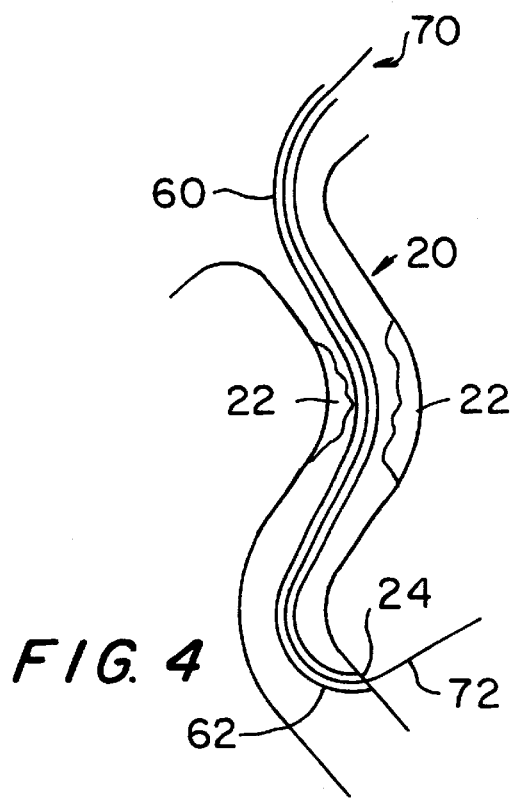
FIG. 4 is still another view similar to FIG. 1 showing a yet later stage in use of the illustrative procedure and apparatus in accordance with the invention.

When the distal portion 62 of structure 60 is properly curved toward the inner surface of the side wall of coronary artery 20 at location 24 as shown in FIG. 3, elongated marker structure 70 is inserted into and along structure 60 as shown in FIG. 4. Distal portion 62 of structure 60 guides the distal portion 72 of marker structure 70 toward the inner surface of the coronary artery side wall. The distal portion 72 of structure 70 is preferably sharply pointed and relatively slender so that it can be easily pushed through the side wall of the coronary artery and any adjacent tissue (e.g., tissue 16 and/or 18 (FIGS. 5–7)) as shown in FIG. 4. Emergence of the distal portion 72 of structure 70 from artery 20 and any adjacent tissue 16 and/or 18 clearly marks location 24 from the outside of artery 20 and adjacent tissue. (See the paragraphs after the next one for features that enhance the findability of distal portion 72.) Because it is relatively easy for the physician to find projecting distal portion 72, it is correspondingly easy for the physician to find the location 24 at which artery 20 requires treatment (e.g., attachment of an end of a bypass conduit for supplying additional blood flow to artery 20 downstream from obstruction 22). After marker structure 70 is in place in the patient as shown in FIG. 4, catheter 60 may be proximally withdrawn from the patient if it is not needed for some other purpose.

An illustrative construction of marker structure 70 is shown in more detail in FIG. 8. In this construction structure 70 is basically a wire, e.g., of stainless steel or nitinol which may be coated with polytetrafluoroethylene to facilitate sliding relative to catheter 60. The proximal portion 70a of structure 70 may have a relatively large cross section to facilitate pushing the structure from a location which is outside the patient (e.g., adjacent a femoral artery entry point of structures 60 and 70). For example, proximal portion 70a may have a diameter of about 0.013 inches. Medial portion 70b may taper in the distal direction from this relatively large diameter to the smaller diameter of distal-most portion 70c. For example, the diameter of portion 70c may be about 0.005 inches, and portion 70b may be about 10 cm in length. Distal-most portion 70c may be about 6 cm in length.

Distal-most portion 70c is preferably radiologically viewable (e.g., radio-opaque) to facilitate proper placement and subsequent detection with the aid of radiology (e.g., fluoroscopy). For example, the radiologic viewability of distal-most portion 70c may be enhanced by coating or joining it with gold, platinum, or silver. As has been mentioned, distal portion 72 is preferably sharply pointed to facilitate tissue penetration. The preferably small cross section of at least distal portion 72 helps the hole made by structure 70 in the wall of coronary artery 20 self-seal and heal when structure 70 is removed from the patient.

In addition to being radiologically viewable, marker structure 70, and especially distal portion 72, is also visually viewable; and its visibility may be enhanced by using a bright or even fluorescent color on it. Alternatively or additionally, marker structure 70 may carry one or more optical fibers for conveying light from a source outside the patient to the vicinity of distal portion 72, where the light is emitted to facilitate visual detection of the marker. This possibility is illustrated by FIG. 10 in which an optical fiber 80 is shown extending along marker structure 70 and emitting light 82. Optical fiber light can of course also be used in applications like those illustrated by FIG. 4.

FIG. 4 shows a marker structure 70 that extends all the way from location 24 proximally out of the patient at the location at which catheter 60 is introduced into the patient. A possible alternative to this type of construction is shown in FIG. 9. In the FIG. 9 alternative a distal portion 72' of marker structure 70 is selectively detachable from a proximal remainder of that structure (not shown in FIG. 9, but similar to the proximal portion of structure 70 shown in FIG. 4). In this way only the portion 72' of marker structure 70 which is actually needed to mark location 24 is left in the patient. The remainder of the apparatus can be completely withdrawn from the patient. Only portion 72' remains in the patient while the patient waits for the further treatment that will make use of the location marking provided by portion 72'. For example, marker portion 72' may be placed in the patient during an angiogram and left in position as shown in FIG. 9 until the patient's surgery takes place. Marker portion 72' may be removably attached to the remainder of marker structure 70 by any suitable means. For example, marker portion 72' may be removably attached by a remotely controlled clamp or collet on the distal end of the remainder of marker structure 70.

FIGS. 4 and 9 show marker structure 70 being used to mark a location 24 that is spaced downstream from obstruction 22. As has been mentioned, marked location 24 may be the site intended for an anastomosis connection of an end of a bypass graft to artery 20. It will be understood that marker structure 70 can be alternatively used to mark a location upstream from obstruction 22, or to mark the location of obstruction 22 itself (i.e., by passing distal portion 72/72' out through the side wall of obstruction 22 and the adjacent side wall of artery 20). FIG. 10 shows marker structure 70 being used to mark a location 24' which is upstream from a total occlusion 22' of artery 20. In cases of total occlusion it is difficult to access the downstream side of the occlusion. But a marker 72 just proximal to the lesion can be helpful (e.g., to give the physician a reference point to compare to previously taken angiograms).

The markers of this invention can be helpful in many types of further procedures, ranging from open body surgery to laparoscopy and ultimately to minimally invasive techniques such as are described in the first three references mentioned above. In any of these further procedures it can be very helpful to have a target location for the further steps clearly marked for the physician. For example, such marking may increase the physician's confidence that he or she will be able to find desired locations along a vessel like artery 20. And by making it easier for the physician to find such locations, the time required for subsequent procedures may be significantly shortened. As has been mentioned, this marking may be detectable visibly, radiologically, or both. When the marker is no longer needed, it may be removed from the patient (e.g., by pulling it proximally out of the patient via its point of entry into the patient).

Figure 11:
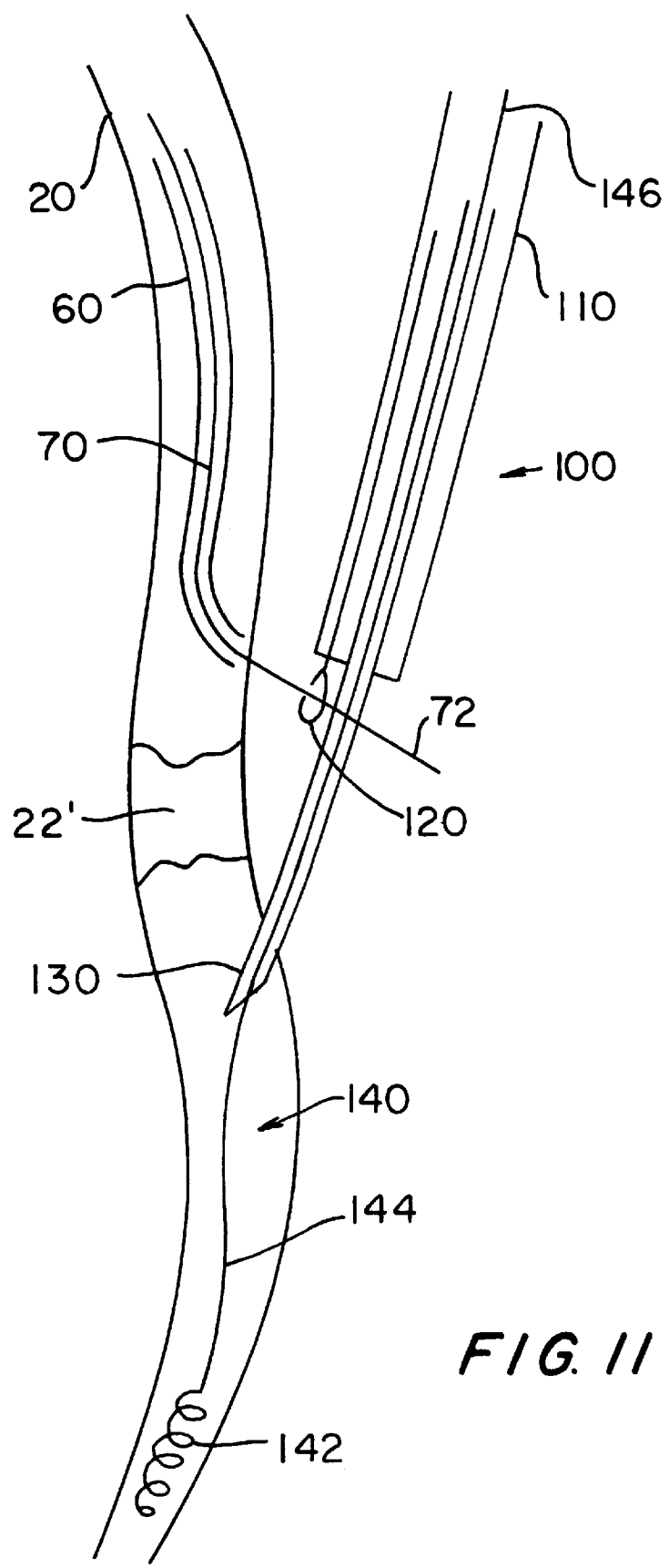
FIG. 11 is another view similar to FIG. 10 showing additional possible uses and apparatus in accordance with this invention.

FIG. 11 illustrates another possible use of a marker in accordance with this invention. In this case marker 70 is additionally used as a locator and anchor for additional instrumentation 100 that is brought up to the outside of vessel 20 after the distal portion 72 of the marker has been extended out through the side wall of the vessel. Instrumentation 100 includes a catheter 110 from which snare 120 and cannula 130 are selectively extendable. Snare 120 is used to snare (grip) the distal portion 72 of marker 70, thereby anchoring the distal portion of catheter 110 relative to the location along vessel 20 at which portion 72 emerges from that vessel. For example, this may be just upstream from total occlusion 22' in vessel 20. With instrumentation 100 thus anchored, cannula 130 is extended distally from the distal end of catheter 110 so that the cannula pierces the side wall of vessel 20 just downstream from total occlusion 22'. Another elongated structure 140 may then be extended distally from the distal end of cannula 130 so that the distal portion of structure 140 continues down along vessel 20 downstream from occlusion 22'. Elongated structure 140 (e.g., a wire) may be used to guide the attachment of a bypass conduit to vessel 20 at the point where structure 140 enters that vessel. For example, this may be done as in either of the two Sullivan et al. references that are mentioned above. It will be apparent that anchoring the distal portion of additional instrumentation 100 to marker portion 72 greatly facilitates getting cannula 130 and therefore elongated structure 140 into vessel 20 at the proper location relative to occlusion 22'. Instrumentation 100 may be brought to the position shown in FIG. 11 either via a surgical opening of the patient or percutaneously (e.g., laparoscopically or intraluminally).

Further considering possible use of apparatus of the type shown in FIG. 11 as an aid to delivering a graft conduit for attachment to vessel 20, elongated structure 140 may include a distal-most portion 142 which is adapted for temporarily securing the distal end of structure 140 in vessel 20. For example, distal-most portion 142 may be a spring coil, a resilient braid (e.g., of nitinol wire strands), an inflatable balloon, or the like. The portion 144 of structure 140 just proximal to distal-most portion 142 may be relatively flexible to facilitate following any curvature of the portion of vessel 20 into which structure 140 is inserted. The still more proximal portion 146 of structure 140 which extends to vessel 20 may be relatively stiff to help provide a stable guideway along which a graft conduit can be delivered to vessel 20. Any of the apparatus shown in FIG. 11 that is not needed for delivery of the graft conduit can be removed or at least retracted prior to delivery of the graft conduit. For example, of the apparatus shown in FIG. 11 only elongated structure 140, positioned as shown in FIG. 11, may be used during graft delivery. All of elements 60, 70, 110, and 120 may therefore be removed or at least retracted prior to delivery of the graft conduit along structure 140.

It will be understood that the foregoing is only illustrative of the principles of the invention, and that various modifications can be made by those skilled in the art without departing from the scope and spirit of the invention. For example, the particular dimensions and materials mentioned above for marker structure 70 are only illustrative, and other dimensions and materials can be used if desired. It will also be understood that the above-described use of the invention in connection with procedures involving a coronary artery is only illustrative, and that the invention can be used at any other suitable location in a patient's circulatory system or other tubular body structures. Similarly, use of the invention as an aid to subsequent bypass graft procedures is only illustrative, and the invention is equally applicable as a preliminary to many other types of patient treatments.

The invention claimed is:

1. A marker structure for use in marking a predetermined location along a patient's tubular body structure comprising:

an elongated longitudinal structure configured for axial insertion into and along a lumen of the tubular body structure to reach the predetermined location, the elongated longitudinal structure having a distal portion configured to pierce a side wall of the tubular body structure at the predetermined location and to project from the side wall through any adjacent tissue outside of the tubular body structure.

2. The marker structure defined in claim 1 wherein at least a portion of the marker structure is radiologically viewable.

3. The marker structure defined in claim 1 where the distal portion has a sharply pointed distal tip to facilitate piercing the side wall of the tubular body structure.

4. The marker structure defined in claim 1 wherein the distal portion is sufficiently flexible so that it can be curved toward the side wall of the tubular body structure at the predetermined location.

5. The marker structure defined in claim 1 wherein the elongated longitudinal structure comprises:

optical fiber configured to convey light axially along the elongated longitudinal structure to the distal portion of that structure where the light is emitted from that structure.

6. Apparatus for inserting a marker through a side wall of a patient's tubular body structure at a predetermined location along that structure comprising:

an elongated longitudinal structure configured for axial insertion into and along a lumen of the tubular body structure to reach the predetermined location; and a marker structure selectively extendable from the elongated longitudinal structure toward and through the side wall of the patient's tubular body structure at the predetermined location to project from the side wall through any adjacent tissue outside of the tubular body structure.

7. The apparatus defined in claim 6 wherein the elongated longitudinal structure has a distal portion which is configured to extend toward the side wall transverse to a longitudinal axis of the lumen of the tubular body structure.

8. The apparatus defined in claim 7 wherein the distal portion of the elongated longitudinal structure is configured to guide the marker structure toward the side wall of the patient's tubular body structure.

9. The apparatus defined in claim 6 wherein the elongated longitudinal structure is configured for guiding into and along the lumen by a guide structure previously inserted into and along the lumen.

10. The apparatus defined in claim 9 wherein the elongated longitudinal structure is further configured to permit proximal withdrawal of the guide structure relative to the elongated longitudinal structure after the elongated longitudinal structure has been inserted into the patient via the guide structure.

11. The apparatus defined in claim 10 wherein the elongated longitudinal structure has a distal portion which is configured to deflect, transversely of a longitudinal axis of the lumen of the tubular body structure, toward the side wall of the tubular body structure in response to withdrawal of the guide structure relative to the elongated longitudinal structure.

12. The apparatus defined in claim 6 wherein the elongated longitudinal structure comprises a tube.

13. The apparatus defined in claim 12 wherein the marker structure is disposed in said tube and is movable relative to the tube substantially parallel to a longitudinal axis of the tube.

14. A method of placing a marker through a side wall of a patient's tubular body structure at a predetermined location along that structure comprising:

inserting an elongated longitudinal structure into and along a lumen of the tubular body structure to reach the predetermined location; and extending a marker structure from the elongated longitudinal structure toward and through the side wall of the patient's tubular body structure at the predetermined location to project from the side wall through any adjacent tissue outside of the tubular body structure.

15. The method defined in claim 14 further comprising:

withdrawing the elongated longitudinal structure from the lumen of the tubular body structure.

16. The method defined in claim 14 further comprising between the inserting and extending:

deflecting a distal portion of the elongated longitudinal structure toward the side wall so that the distal portion of the elongated longitudinal structure will guide the marker structure toward the side wall when the extending is performed.

17. The method defined in claim 14 wherein the marker structure includes selectively separable distal and proximal portions, wherein the distal portion is extended through the side wall in the extending, and wherein after the extending the method further comprises:

separating the distal and proximal portions from one another.

18. The method defined in claim 17 further comprising after the separating:

withdrawing the proximal portion from the patient.

19. The method defined in claim 14 wherein the predetermined location is distal of a partial obstruction in the tubular body structure, and wherein the inserting comprises:

passing the elongated longitudinal structure through the obstruction in order to reach the predetermined location.

20. Apparatus for making an entry into a tubular body conduit of a patient from outside that conduit comprising:

first instrumentation which is insertable axially into and along the interior of the conduit, the first instrumentation including a marker structure which is selectively extendable out of the conduit through a side wall of the conduit; and second instrumentation which is configured to approach the outside of the conduit and interengage with the marker structure extending out of the conduit through the side wall of the conduit, the second instrumentation including a tissue penetrating structure which is selectively extendable relative to a remainder of the second instrumentation and which is configured to pass through the side wall of the conduit at a location spaced from the marker structure penetration of the side wall of the conduit.

21. The apparatus defined in claim 20 wherein the second instrumentation comprises:

a snare structure configured to selectively grip the marker structure extending out of the conduit through the side wall of the conduit.

22. The apparatus defined in claim 20 wherein the tissue penetrating structure comprises:
   a cannula.

23. The apparatus defined in claim 22 wherein the tissue penetrating structure further comprises:
   an elongated structure selectively extendable through the cannula.

24. A method for making an entry into a tubular body conduit of a patient from outside that conduit comprising:
   extending a marker structure along the interior of the conduit and out through a side wall of the conduit;
   attaching instrumentation which is outside the conduit to a portion of the marker structure which extends out through the side wall of the conduit; and
   extending tissue penetrating structure from the instrumentation so that the tissue penetrating structure passes through the side wall of the conduit at a location which is spaced from the extension of the marker structure through the side wall of the conduit.

25. The method defined in claim 24 wherein the conduit contains an obstruction at an axial location along said conduit's length, and wherein the extension of the marker structure through the side wall of the conduit and the passage of the tissue penetrating structure through the side wall of the conduit are spaced from one another axially along the conduit on respective opposite sides of the obstruction.

26. The method defined in claim 24 wherein the tissue penetrating structure is a cannula, and wherein the method further comprises:
   extending a longitudinal structure through the cannula into the interior of the conduit.

* * * * *